United States Patent [19]

Raymond et al.

[11] Patent Number: 4,698,431

[45] Date of Patent: Oct. 6, 1987

[54] HYDROXYPYRIDONATE CHELATING AGENTS

[75] Inventors: Kenneth N. Raymond, Berkeley, Calif.; Robert C. Scarrow, Minneapolis, Minn.; David L. White, Oakland, Calif.

[73] Assignee: The United States of America as represented by the United States Department of Energy, Washington, D.C.

[21] Appl. No.: 796,815

[22] Filed: Nov. 12, 1985

[51] Int. Cl.[4] .......................................... C07D 213/90
[52] U.S. Cl. ..................................... 546/298; 546/261
[58] Field of Search ........................................ 546/298

[56] References Cited

U.S. PATENT DOCUMENTS

| | | | |
|---|---|---|---|
| 3,864,334 | 2/1975 | Pallos | 546/268 |
| 3,928,616 | 12/1975 | Pallos | 514/348 |
| 4,063,927 | 12/1977 | Otten et al. | 71/94 |
| 4,181,654 | 1/1980 | Weitl et al. | 540/474 |
| 4,293,542 | 10/1981 | Lang et al. | 424/47 |
| 4,309,305 | 1/1982 | Weitl et al. | 252/631 |
| 4,396,766 | 8/1983 | Farmer, Jr. et al. | 546/6 |
| 4,397,867 | 8/1983 | Blake | 514/575 |
| 4,419,365 | 12/1983 | McLachlan | 514/575 |
| 4,442,305 | 4/1984 | Weitl et al. | 562/451 |
| 4,530,963 | 7/1985 | DeVoe et al. | 525/54.1 |
| 4,543,213 | 9/1985 | Weitl et al. | 540/474 |

OTHER PUBLICATIONS

Scarrow et al., CA 102: 124493g.
Raymond et al., CA 103: 192911n.
Durbin, P. W. et al., "Kinetics of Plutonium Deposition in the Mouse", Ann. Rpt. 1983-4, Biology and Medicine Division, Lawrence Berkeley Lab. (Apr. 1985).
Durbin, P. W. et al., "New Sequestering Agents for the Actinides . . . ", Ann. Rpt. 1983-4, Biology and Medicine Division, Lawrence Berkeley Lab. (Apr. 1985).
Raymond, K. N., "Specific Sequestering Agents for Iron and Actinides," in *Environmental Inorganic Chemistry* (VCH Publishers, Inc. 1985).
Riley, P. E. et al., "Specific Sequestering Agents for the Actinides.9.Synthesis of Metal Complexes of 1-Hydroxy-2-Pyridinone . . . ," *Inorganic Chemistry*, 22 (1983), pp. 3940 et seq.
Scarrow, R. C. et al., "Ferric Ion Sequestering Agents . . . ," *Inorganic Chemistry*, 24 (1985), pp. 954 et seq.

Primary Examiner—Jane T. Fan
Attorney, Agent, or Firm—Harold M. Dixon; L. E. Carnahan; Judson R. Hightower

[57] ABSTRACT

Chelating agents having 1-hydroxy-2-pyridinone (HOPO) and related moieties incorporated within their structures, including polydentate HOPO-substituted polyamines such as spermidine and spermine, and HOPO-substituted desferrioxamine. The chelating agents are useful in selectively removing certain cations from solution, and are particularly useful as ferric ion and actinide chelators. Novel syntheses of the chelating agents are provided.

2 Claims, No Drawings

HYDROXYPYRIDONATE CHELATING AGENTS

FIELD OF THE INVENTION

This invention relates generally to novel chelating agents, and more specifically relates to chelating agents which incorporate within their structures 1-hydroxy-2-pyridinone moieties and analogs thereof. The invention also relates to methods of synthesizing and using such chelating agents.

BACKGROUND OF THE INVENTION

The Government has rights in this invention pursuant to Contract No. DE-AC03-76SF-00098 awarded by the U.S. Department of Energy.

Siderophores are highly selective ferric chelating agents synthesized and released by microorganisms to ensure the presence of sufficient iron for survival, in readily usable, i.e. solubilized, form. The preparation of synthetic analogs of siderophores is of some interest, as such analogs could have important potential applications as clinical iron removal agents, particularly for patients who suffer from blood diseases such as beta-thalassemia, the treatment of which requires the regular transfusion of whole blood and results in the accumulation of massive tissue iron deposits. Because of the similarity in coordination properties between the ferric ion and the tetravalent actinides, synthetic analogs of siderophores are also potential chelators of tetravalent actinides, which present significant biological hazards associated with nuclear technology. Normally, such actinide chelating agents will be octadentate ligands, as opposed to the generally hexadentate siderophores. Other uses, such as radionuclide chelation in nuclear medicine applications, for example, are also clearly possible.

The metal-binding ligands of siderophores are usually either catechols (dihydrobenzene analogues; Formula 1) or hydroxamic acids (Formula 2).

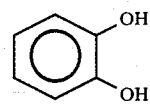

Formula 1

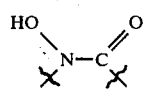

Formula 2

The siderophore enterobactin, for example, incorporates three catechol groups as a hexadentate ligand. Synthetic analogs of catechol-based siderophores are also known. See, e.g., U.S. Pat. No. 4,530,963 to DeVoe et al., issued July 23, 1985. However, the weak acidity of catechol and the required loss of two protons per catechol group at or about neutral pH limit the effectiveness of catechol-based ligands. It is therefore desirable to provide a medicinally useful chelating agent having a lower $pK_a$ that is more versatile than catechol-based compounds. Uninegative ligands, i.e., ligands having a single negative charge at neutral pH, are particularly desirable, in contrast to the corresponding highly charged ferric and plutonium catechol complexes. The importance of both $pK_a$ and a monoprotic acid ligand is illustrated by the exponential nature of the proton-dependent metal-ligand complex formation constant (Eq. 1).

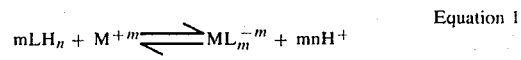

Equation 1

$$K_{complex\ formation} = \frac{[ML_m^{-m}][H^+]^{mn}}{[LH_n]^m[M^+]}$$

Derivatives of 1-hydroxy-2-pyridinone (Formula 3; "HOPO") are of particular interest, since the ligand and its mono-anion (Formula 4) have a zwitterionic resonance form (Formula 5) that is isoelectronic with the catechol dianion. The abbreviation "HOPO" will hereinafter be used to include 1-hydroxy-2-pyridinone analogues as well as isomers of tautomers thereof, in either protonated or deprotonated form.

The HOPO structure possesses some important synthetic advantages. The 6-carboxylic acid structure (Formula 6) can be made in a straightforward manner, and further, the placement of functional groups at the 1, 2, and 6 positions makes possible the activation of the carboxylic acid moiety without the need for a protecting group at the N-hydroxyl position. HOPO derivatives provided by the present invention also have the desired low $pK_a$ and are uninegative at neutral pH.

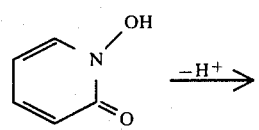

Formula 3

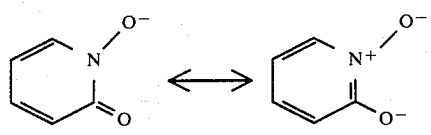

Formula 4    Formula 5

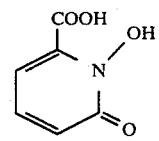

Formula 6

SUMMARY OF THE INVENTION

Accordingly, it is an object of the present invention to provide novel chelating agents which will form highly stable complexes with cations such as Fe (III) and Pu (IV), and which will promote significant excretion of such cations.

It is another object of the invention to provide chelating agents which are relatively acidic and incorporate monoprotic ligand groups.

It is still another object of the invention to provide chelating agents which incorporate 1-hydroxy-2-pyridinone moieties within their structures.

It is a further object of the invention to provide methods of synthesizing the novel HOPO-based chelating agents.

It is still a further object of the invention to provide methods of using the novel chelating agents.

In one aspect of the present invention, novel chelating agents are provided which include HOPO-based monomers and dimers as well as larger structures such as HOPO-substituted desferrioxamine. In other aspects of the invention, novel methods of synthesizing the HOPO-derived chelating agents are provided, as are methods of using the novel compounds.

DETAILED DESCRIPTION OF THE INVENTION

The present invention first of all provides novel chelating agents capable of forming stable complexes with certain cations and selectively removing those cations from solution. The inventors herein have demonstrated the effectiveness of novel chelating agents having 1-hydroxy-2-pyridinone ("HOPO") and related moieties incorporated within their structures. HOPO-based compounds provide a number of advantages, and demonstrate superior utility as chelating agents having important pharmaceutical applications. In contrast to their catechol analogues, the novel HOPO-based chelators are uninegative at neutral pH and are soluble in water without the addition of carboxylic or sulfonic acid solubilizing groups. The solubility properties of the HOPO-substituted compounds in combination with their relatively low $pK_a$'s make them effective oral agents; present therapeutic agents, by contrast, are given by injection. The new HOPO compounds display high binding constants for ferric ion, on the order of $10^{26}$ to $10^{27}$ $M^{-3}$ for the tris (HOPO) Fe(III) comlexes, and are thus effective ligands for iron as well as for the other ions with similar coordination properties (e.g., the actinides).

Monomeric compounds of the invention include those given by the structure of Formula 7.

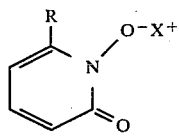

Formula 7

In Formula 7, R is either an amide (Formula 7B) or a carboxylic acid (Formula 7A) moiety. In the carboxylic acid form, the compound is 1-hydroxy-2-pyridinone-6-carboxylic acid ("HOPO—$CO_2H$"). In the amide form, R has the structure

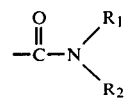

Formula 8 where $R_1$ and $R_2$ are preferably alkyl, aryl, or arylalkyl, and more preferably are either —H, —$CH_3$, —$CH_2CH_3$, or —$CH_2$—$\phi$. In both forms, X may be hydrogen, an alkali metal ion, or a quaternary ammonium ion such as $N(CH_3)_4^+$.

Chelating agents of the present invention which incorporate two HOPO-type structures are given by Formula 9.

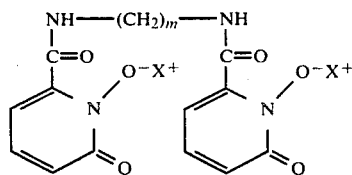

Formula 9

In Formula 9, X is as given above for the monomers of Formula 7, and m is an integer between one and twenty. In a particularly preferred form, m is three, and the structure is "3-HOPOCAM" (1-hydroxy-2-pyridinone structures separated by three methylene groups, somewhat analogous in structure to previously known catechoyl amide, or "CAM", sequestering agents).

Other chelating agents provided by the present invention include a number of HOPO-substituted amine and polyamine structures. Examples of these HOPO-substituted compounds include those structures given by Formulae 10, 11, 12, and 13.

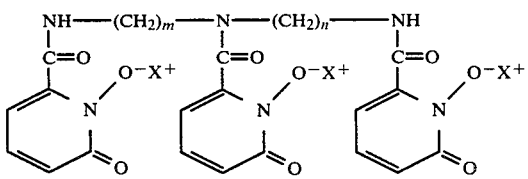

Formula 10

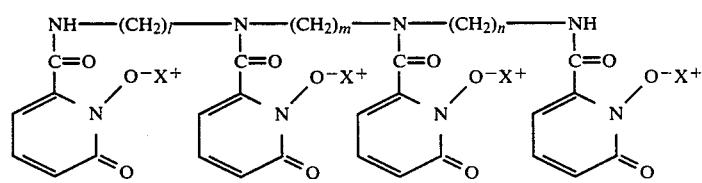

Formula 11

Formula 12

[structure: benzene ring with three −CH₂−NHC(O)−Z groups]

Formula 13

$$CH_3-\underset{O}{\overset{||}{C}}-\underset{OH}{\overset{|}{N}}-(CH_2)_j-NH-\overset{||}{\underset{O}{C}}-(CH_2)_k-\overset{||}{\underset{O}{C}}-\underset{OH}{\overset{|}{N}}-(CH_2)_l-NH-\overset{||}{\underset{O}{C}}-(CH_2)_m-\overset{||}{\underset{O}{C}}-\underset{OH}{\overset{|}{N}}-(CH_2)_n-NH$$

[terminal group: −C(=O)−N(O⁻X⁺)− attached to pyridinone ring]

In Formulae 10 through 13, j, k, l, m and n are preferably integers between one and twenty. In a particularly preferred embodiment of the compound given by Formula 10, m is three, n is four, and the structure is "3,4-HOPOCAM," a HOPO-substituted spermidine analogue. With regard to Formula 11, a particularly preferred structure is "3,4,3-HOPOCAM," a HOPO-substituted spermine analogue, where l and n are three, and m is four. Formula 12 gives a HOPO-substituted tris aminomethylbenzene analogue ("HOPO-MECAM"), with the "Z" moieties preferably being HOPO groups. Formula 13 gives a HOPO-substituted analogue of desferrioxamine-B, in which j, l, and n are preferably two, while k and m are preferably five.

This substituted desferrioxamine (known variously as "DF," "DFO," "DF-B" and "DFOM") compound will hereinafter be referred to as "DFHOPOCAM" (desferrioxamine 1-hydroxy-2-pyridinone analogue of the catechoyl amide structure). This latter compound represents a particularly preferred embodiment of the invention, as it has been demonstrated to be extremely effective both in ferric ion chelation and in the decorporation of actinides such as Pu(IV).

The chelating agents of this invention also include amine compounds which in addition to having at least one HOPO ligand are also substituted with catechol and catechol analogues. Thus, in the compounds of Formulae 10–13 above, the HOPO substituents could be replaced with the either of the structures given by Formulae 14 or 15, so long as one HOPO substituent remains present on the chelating structure.

Formula 14

[catechol structure with C=O, two OH groups]

Formula 15

[catechol structure with C=O, two OH groups, and COO⁻X⁺]

Also included in the present invention are chelating agents having polymeric backbones and at least one amine functionality to which a HOPO substituent is bonded through an amide-type linkage. Examples of suitable polymers here include poly(styrene-divinylbenzene), agarose (manufactured by Bio-Rad Corp., Richmond, CA, under the name "Affi-Gel"), and polyacrylamide.

The present invention also relates to novel methods of synthesizing the aforementioned chelating agents, as outlined below.

The monomeric compounds shown in Formula 7 may be synthesized according to Scheme I.

Scheme I

Formula 16: [6-bromo-pyridine-2-carboxylic acid] $\xrightarrow[CF_3COOH]{H_2O_2}$

Formula 17: [N-oxide of 6-bromo-pyridine-2-carboxylic acid] $\xrightarrow{KOH}$

Formula 7A: [1-hydroxy-6-oxo-1,6-dihydropyridine-2-carboxylic acid] $\xrightarrow[(2) NHR_1R_2]{(1) COCl_2}$ Formula 7B: [1-hydroxy-6-oxo-1,6-dihydropyridine-2-carboxamide, CONR₁R₂]

The 6-carboxylic acid derivative (Formula 7A) of 1-hydroxy-2-pyridinone is prepared from a 6-halopyridine-2-carboxylic acid (Formula 16; the compound is preferably 6-bromo, as shown) as follows. The compound of Formula 16 is oxidized to yield the 1-oxide derivative (Formula 17); preferred oxidizing agents include a mixture of trifluoroacetic acid and hydrogen peroxide. The 1-oxide of Formula 17 is then dissolved in a hydroxide solution such as aqueous potassium hydroxide and allowed to remain for at least one hour at an elevated temperature of at least about 60° C. The solution is then cooled and treated with acid; the 6-carboxylic acid (Formula 7A) may then be isolated, e.g. by filtration, purified, and dried (see Example 1).

The HOPO amide monomer shown in Formula 7B may then be prepared from the 6-carboxylic acid compound of Formula 7A as follows. A quantity of the 6-carboxylic acid derivative is suspended in an inert and preferably polar solvent such as tetrahydrofuran (THF) or other ethereal solvents. A preferred ratio of 7A to solvent is about 1:10. Phosgene gas is bubbled in until the suspended starting material is dissolved; alternatively, compounds which generate phosgene gas may be admixed into the solution. After a reaction period of between about 5 min. and about 30 min. at a temperature ranging from about 10° to about 80° C., preferably approximating 25° C., volatiles, including any excess phosgene, are removed from the reaction mixture in vacuo. The viscous residue obtained is dissolved in an inert, organic, and preferably polar solvent, and added to a solution of amine. An amine of formula $NHR_1R_2$ will provide the general structure of Formula 7B; dimethylamine, for example, will yield N,N'-dimethyl-1-hydroxy-2(1H)-pyridinone-6-carboxamide (see Example 2). After reaction with the amine is allowed to proceed at room temperature for at least about several hours, the product of Formula 7B is isolated, purified, and dried. (The inventors herein postulate that the intermediate structure involved in the foregoing reaction is a cyclic anhydride having the structure

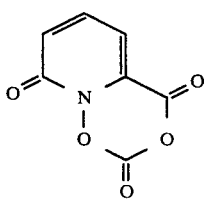

Formula 18 which reacts with the amine compound to yield the HOPO-amide derivative.)

It is also possible to carry out the above reaction producing the HOPO-amide monomer of Formula 7B using thionyl chloride. See, e.g., Scarrow et al., "Ferric Ion Sequestering Agents. 13. Synthesis, Structures and Thermodynamics of Complexation of Cobalt (III) and Iron (III) Tris Complexes of Several Chelating Hydroxypyridinones," *J. Inorg. Chem.* 24 (6), 954–967, at 956 (1985), the disclosure of which is hereby incorporated by reference in its entirety. It has proved quite difficult, however, to prepare multiply HOPO-substituted compounds using thionyl chloride, primarily because of solubility limitations. Accordingly, the inventors herein propose a novel synthesis whereby amine compounds having a plurality of HOPO ligands incorporated within their structures are provided.

These polydentate HOPO-substituted amines are prepared starting from the 6-carboxylic acid HOPO monomer of Formula 7A, which is dissolved in an N,N'-dialkylamide such as dimethylacetamide (DMAA) or dimethylformamide (DMF). The solution is cooled in an ice bath, and an approximately equimolar amount of phosgene in an inert, organic, and preferably polar solvent (e.g., ethereal solvents such as THF) is added. The resulting reaction is mildly exothermic and produces some gas evolution. After at least about five minutes, a stoichiometric amount of triethylamine is added to the reaction mixture, producing a complex presumably having the structure

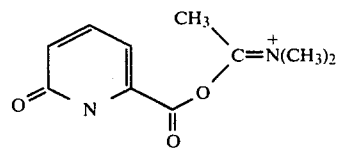

Formula 19

The reaction mixture is stirred for at least about 5 min., preferably about 30 min., at a temperature ranging from about 5°–60° C., and preferably below about 20° C. A predetermined amount of the amine compound which will provide the "backbone" of the chelating agent is then added and the reaction mixture is stirred for at least 1 hr. at room temperature to ensure complete reaction. While any number of amines can be used in this reaction to effect production of HOPO-substituted chelating agents, preferred amines are those which correspond to the structures of Formulae 10–13. Particularly preferred amines are the polyamines 1,3-diaminopropane ($NH_2$—$(CH_2)_3$—$NH_2$), spermidine ($NH_2$—$(CH_2)_3$—$NH$—$(CH_2)_4$—$NH_2$), spermine ($NH_2$—$(CH_2)_3$—$NH$—$(CH_2)_4$—$NH$—$(CH_2)_3$—$NH_2$), tris aminomethylbenzene (see Formula 12) and the polymeric monoamine desferrioxamine (see Formula 13). The reaction mixture is filtered to remove precipitated $Et_3N.HCl$, and the solvent is removed. The viscous residue is purified, preferably by extraction and/or column chromatography. Mono- and bis [1-hydroxy-2(1H)-6-carbonyl-]amines prepared by this procedure are best recrystallized from water, while tris- and tetrakis-compounds (generally hygroscopic, glassy solids) are best purified by high performance liquid chromatography (HPLC).

Other amines which may be used in the above synthetic procedure include compounds generally given by Formulae 10–13 but having one or more catechol-type ligands (see Formulae 14 and 15) in addition to at least one HOPO group. Hydrocarbon polymers having at least one amino group may also be used (e.g., agarose, polyacrylamide, and other similar compounds).

Properties of the novel compounds:

Physical Properties: The mono- and bis-HOPO compounds (e.g., Formulae 7 and 8) are white to very pale yellow solids. While not necessarily crystalline, they can be easily isolated as freely flowing powders with sharp melting points. As the number of pendent HOPO moieties is increased, however, the solids become more and more hygroscopic, glassy in nature, and difficult to characterize. The most distinctive feature of their NMR spectra is the set of three doublets in the aromatic region arising from the HOPO ring protons (see Examples 5 and 6). Their IR spectra display a strong band at ca. 1650 cm.$^{-1}$ due to overlapping amide and ring carbonyl absorptions. A ring stretching band at 1570 cm$^{-1}$ is also observed. However, the HOPO derivative of desferrioxamine, displays a maximum at 1622 cm$^{-1}$ presumably due to overlap with the hydroxamic acid carbonyl bands.

Chemical Properties. The novel HOPO-substituted amine compounds are moderately to very soluble in water (on the order of 1 g/10 ml at room temperature, 5g/10 ml at 80° C.). They are weakly acidic (having $pK_a$'s on the order of 5), and the pH of saturated aqueous solution is typically about three. They form complexes with metal ions, e.g., $Th^{+4}$, $Zn^{+2}$, and $Fe^{+3}$.

As mentioned above, the compounds of the present invention may be used in a variety of applications. The compounds are primarily useful in selectively removing cations from solution, and are particularly useful with +2, +3 and +4 cations. For example, these HOPO-substituted compounds are exemplary ferric ion chelators and are thus useful in the removal of excess iron from the body. For this latter application, preferred doses range from about 20 mg/kg to about 200 mg/kg. The major route of excretion is primarily through the kidneys; the relative potency here (highest fraction of iron excreted) is greatest for the HOPO-substituted desferrioxamine (DFHOPOCAM; see Example 8). (Iron removal from transferrin is also quite rapid—see Example 11.)

The novel chelators are also effective chemical agents for decorporation of actinides and other chemically similar ions, as they have been shown to promote significant excretion of actinides such as Pu(IV). Again, while all of the inventive compounds are quite effective in this regard, DFHOPOCAM seems to produce the most effective removal of such ions (see Example 12).

Experimental Methods:

Infrared spectra were obtained using a Perkin-Elmer Model 283 spectrophotometer. NMR spectra were obtained on Jeol FX-90Q (90 MHz) or UCB-250 (250 MHz) spectrometers. Electron impact ionization (EI) mass spectra were obtained using an AEI MS-12 instrument, while a Finnigan 4000 instrument provided CI mass spectra using methane. A Kratos MS-50 Mass Spectrometer using a xenon beam was employed to acquire fast atom bombardment ionization (+FAB) mass spectra. Microanalyses were performed by the Microanalytical Laboratory, Chemistry Dept., University of California, Berkeley, Calif. 94720. C, H, and N analyses were within 0.4% of the calculated values for all new compounds, unless otherwise noted.

HPLC was performed on a Beckman-Altex Model 340 system using an Altex Ultrasphere ODS precolumn (4.6 mm id × 40 mm) and column (4.6 mm id × 150 mm) for analytical work. A similar 10 mm id × 250 mm column was used for preparative chromatography. Unless otherwise stated, the mobile phase was a methanol-water gradient (0 to 100% MeOH over 10 minutes), with each component 0.025M in formic acid (pH 2.8).

1-Hydroxy-2-(1H)-pyridinone-6-carboxylic acid was prepared as described in Example 1. Triethylamine, THF, and N,N-dimethylacetamide (DMAA) were purified by distillation under nitrogen from sodium, potassium benzophenone ketyl, and phosphorus pentoxide, respectively. Spermine and spermidine were obtained from The Ames Laboratories, Inc., Milford, CT. Desferrioxamine was obtained from Ciba-Geigy ("Desferal," a trademark of Ciba-Geigy Corp.). Other organic reagents were purchased from the Aldrich Chemical Co. and used without further purification.

Solutions of phosgene in THF were prepared by bubbling the gas into a weighed quantity of anhydrous solvent cooled in an ice bath until the desired mass had been dissolved. The titer of this solution was determined by reacting an aliquot with excess aniline in THF and quantifying the resulting carbanilide by HPLC.

EXAMPLE 1

Preparation of 1-hydroxy-2(1H)-pyridinone-6-carboxylic acid (Formula 7A): A 9.7 g (0.048 mol.) portion of 6-bromopyridine-2-carboxylic acid was added to a solution of 125 ml of $CF_3COOH$ and 18 ml of 30% $H_2O_2$ and heated to 80° C. for 6.5 h. The reaction mixture was concentrated to ca. 25 ml by rotary evaporation and then added to 1 l of water. The product immediately precipitated as a finely divided, white crystalline solid. It was isolated by filtration, washed with water, and dried in vacuo. This yielded 10.2 g of product, 2-bromopyridine-6-carboxylic acid (Formula 16), mp 180° C. dec. Anal. Calcd. for $C_6H_4BrNO_3$: C, 33.05; H, 1.85; Br, 36.65; N, 6.43. Found: C, 33.30; H, 1.88; Br, 36.37; N, 6.52.

A 10.1 g (0.046 mol.) portion of the 2-bromopyridine-6-carboxylic acid prepared above was dissolved in 175 ml of a 10% aqueous KOH solution, and the resulting solution was maintained at 80° C. overnight and then cooled in an ice bath and treated with 85 ml of concentrated HCl. The white suspended solid was isolated by filtration, washed with dilute HCl followed by three 15-ml portions of water, and then dried in vacuo to yield 6.21 g (86.4%) of 1-hydroxy-2(1H)-pyridinone-6-carboxylic acid (Formula 7A), mp 216° C. dec. Anal. Calcd. for $C_6H_5NO_4$: C, 46.45; H, 3.25; N, 9.03. Found: C, 46.29; H, 3.26; N, 8.96.

EXAMPLE 2

Preparation of N,N'-dimethyl-1-hydroxy-2(1H)-pyridinone-6-carboxamide (Formula 7B; $R_1=R_2=CH_3$): A 3-neck 25 ml flask equipped with a magnetic stirrer, subsurface gas inlet, and gas outlet was charged with 10 ml of THF and 0.60 g (3.9 mmoles) of 1-hydroxy-2(1H)-pyridinone-6-carboxylic acid (Formula 7A). Phosgene gas was bubbled in until the suspended starting material had dissolved. After a reaction period of 15 min at 25° C., volatiles were removed from the reaction mixture in vacuo. The viscous residue was dissolved in THF, and this solution was added to 20 ml of THF saturated with dimethylamine. Additional gas was bubbled into the solution during the addition to ensure an excess. The resulting suspension was filtered to remove $Et_3N.HCl$, and solvent and excess amine were removed on a rotary evaporator. The residue was dissolved in 7 ml of water, and this solution was applied to a 1.45 cm id × 14 cm long column of AG 50-X8 ion exchange resin (Bio-Rad) in the H+ form and eluted with water. HCl appeared first, followed by a light yellow fraction that gave a red color when treated with ferric ion. Removal of water from the latter fraction left 0.42 g (60%) of light yellow product (Formula 7B), mp 165°–168° C. EI Mass. Spec.: 182 (M+, 1), 166 (88), 122 (49), 72 (92). $^1$H NMR: δ 2.95 (s; 3; $NCH_3$), 3.05 (s; 3; $NCH_3$), 4.77 (bs; 1; NOH), 6.29 (dd; 1; J=1.6, 7.03; pyr-3- or 5-H), 6.59 (dd; 1; J=1.6, 9.22; pyr-5- or 3-H), 7.39 (dd; 1; J=7.03, 9.22; pyr-4-H) (in $Me_2SO$-$D_6$).

EXAMPLE 3

Preparation of a HOPO amide monomer (Formula 7B; $R_1=H$, $R_2=$benzyl): A dry 250 ml 3-neck round-bottom flask equipped with a magnetic stirrer, gas inlet, addition funnel, and thermometer was flushed with nitrogen and charged with 3.10 g (20 mmoles) of 1-hydroxy-2(1H)-pyridinone-6-carboxylic acid (Formula 7A) and 50 ml of DMAA. The solution was cooled in an ice bath and then treated dropwise with 21 mmoles of phosgene in THF solution. The resulting mildly exothermic reaction produced some gas evolution and a bright yellow reaction mixture. The addition of 8.71 g (86 mmoles) of triethylamine also gave an exothermic reaction, and a white precipitate was formed. After being stirred for 30 min. at 5°–10° C., this suspension was treated with 16 meq of benzylamine. The resulting mixture was allowed to stir overnight at room temperature. The reaction mixture was then filtered to remove precipitated $Et_3N.HCl$, and solvent was removed from the filtrate on a rotary evaporator. The viscous, amber residue was partitioned between 50 ml each of chloroform and dilute aqueous $NH_3$ (pH 10). The chloroform extract, containing non-polar by-products, was discarded; the aqueous phase was concentrated to about 20 ml. This solution then was chromatographed on a 2.5 cm id×20 cm long column of Ag 50-X8 ion exchange resin in the $H^+$ form eluting with water. HCl eluted first, followed immediately by an acidic (pH 1.5) yellow fraction that gave a bright red-orange precipitate upon reaction with $Fe^{+3}$. This fraction contained essentially only the carboxylic acid of Formula 7A, and about 0.6 g (20%) could be recovered upon evaporation. The pH of the eluant then began to rise to about 3, and the color of the $Fe^{+3}$ spot test became brown-red. This signaled elution of the product-containing fraction. This was usually contaminated with small amounts of 7A, as well as by-products. These contaminants were removed upon recrystallization in water, yielding a pure product, mp 129°–130° C. +FAB Mass. Spec.: 259 ($M^+ + Na$, 3), 245)$M^+ + H$, 100), 229 (79). $^1H$ NMR: δ 4.40 (bs; 1; $NCH_2$), 4.47 (bs; 1; $NCH_2$), 6.34 (d; 1; J=6.2; pyr-3- or 5-H), 6.57 (d; 1; J=7.8; pyr-5- or 3-H), 7.32 (m; 6; $C_6H_5$ and pyr-4-H), 9.37 (bt; 1; J=7; CONH) (in $Me_2SO-D_6$).

EXAMPLE 4

Preparation of 3-HOPOCAM (Formula 9; m=3, X=Na): A procedure identical to that carried out in Example 3 was followed; however, the benzylamine used in that procedure was replaced by 1,3-diaminopropane ($H_2N$-$(CH_2)_3$-$NH_2$). The product, 3-HOPOCAM, was recrystallized in water and obtained in about a 50% yield, mp 206°–207° C. +FAB Mass. Spec.: 349 ($M^+ + H$, 100), 333 (61), 317 (15). $^1H$ NMR: δ 1.76 (q; 2; J=6.5; $CH_2CH_2CH_2$), 3.26 (d(t); 4; J=4.2, 6.5; $NHCH_2CH_2$), 6.30 (dd; 2; J=1.6, 6.5; pyr-3- or 5-H), 6.56 (dd; 2; J=1.6, 8.8; pyr-5- or 3-H), 7.39 (dd; 2; J=6.5, 8.8; pyr-4-H) (in $Me_2SO-D_6$).

EXAMPLE 5

Preparation of 3,4-HOPOCAM (Formula 10; m=3, n=4, X=Na): A procedure identical to that of the previous two examples was followed, with the exception that the amine used in this example was spermidine. The product, 3,4-HOPOCAM, was isolated by HPLC and obtained in about a 34% yield, mp 130°–135° C. +FAB Mass. Spec.: 557 ($M^+ + H$, 100), 541 (65), 525 (19), 509 (4). $^1H$ NMR: δ 1.55 (bm; 6; $CH_2CH_2CH_2$), 3.2–3.4 (bm; 8; $CONCH_2$), 6.23 (m; 3; pyr-3- or 5-H), 6.55 (d; 3; J=8, pyr-5- or 3-H), 7.39 (t; 3; J=8, pyr-4-H), 8.74 (t; 2; J=7; CONH) (in $Me_2SO-D_6$).

EXAMPLE 6

Preparation of 3,4,3-HOPOCAM (Formula 11; l=n=3, m=4, R' is HOPO): The procedures of Examples 3, 4, and 5 was again followed, with spermidine providing the amine backbone. The product, 3,4,3-HOPOCAM, was isolated by HPLC and obtained in about a 15% yield. M.p. 135° C. +FAB Mass. Spec.: 773 ($M^+ + Na$, 5), 751 ($M^+ + H$, 86), 735 (100). $^1H$ NMR: δ 1.73 (bm; 8; $CH_2CH_2CH_2$), 2.8–3.7 (bm; 12; $CONCH_2$), 6.18 (m; 4; pyr-3- or 5-H), 6.53 (719 (47), 703 (22) (d; 4; J=7; pyr-5- or 3-H), 7.38 (t; 4; J=7; pyr-4-H), 8.75 (m; 2; CONH) 2.8 (in $Me_2SO-D_6$).

EXAMPLE 7

Preparation of HOPOMECAM (Formula 12; Z=HOPO): The procedure of the previous four examples was followed, with tris aminomethylbenzene as the amine to be substituted with three HOPO ligands. The product, HOPOMECAM, was purified by HPLC and isolated in about a 17% yield. M.p. 135° C. dec. +FAB Mass. Spec.: 577 ($M^+ + H$, 100), 561 (50), 545 (31). $^1H$ NMR: δ 4.41 (s; 3; $CONCH_2$), 4.47 (s; 3; $CONCH_2$), 6.36 (dd; 3; J=1, 6.9; pyr-3- or 5-H), 6.57 (dd; 3; J=1, 8.5; pyr-5- or 3-H), 7.19 (s; 3; $C_6H_3$), 7.37 (dd; 3; J=6.9, 8.5; pyr-4-H), 9.35 (t; 3; J=5).

EXAMPLE 8

Preparation of DFHOPOCAM (Formula 13; j=l=n=2, k=m=5): The procedure of the previous example was followed, with desferrioxamine as the amine backbone. The product, DFHOPOCAM, was recrystallized in water and obtained in about a 56% yield. M.p. 141°–143° C. +FAB Mass. Spec.: 720 ($M^+ + Na$, 23), 698 ($M^+ + H$, 100), 682 (48). $^1H$ NMR: δ 1.14–1.86 (m; 18; $CH_2CH_2CH_2$), 2.08 (s; 3; $COCH_3$), 2.44 (t; 4; J=5.9; $NHCOCH_2$), 2.74 (t; 4; J=5.9; $NOHCOCH_2$), 3.16 (t; 4; J=6.4; $CONHCH_2$), 3.59 (t; 6; J=6.9; $CONOHCH_2$), 6.71 (d; 2; J=8.0; pyr-3- and 5-H), 7.46 (t; 1; J=8.0; pyr-4-H) (in $CD_3OD$).

EXAMPLE 9

Iron Removal Bioassay in Mice

DFHOPOCAM was tested for its effectiveness in removing iron from iron-loaded mice. The mice tested had undergone three transfusions over five days of heat-treated canine red blood cells. Both low i.p. doses (about 20 mg/kg) and high doses (about 200 mg/kg) were administered, in aqueous solution. Analysis of daily excreta during a five-day recovery period disclosed reversal of most of the damage to excretory pathways resulting from the excess metabolic iron.

At the lower dose, behavior was not affected, and necropsy failed to reveal any changes in the size or color of major organs. A favorable 11% decline in splenic iron (see Table 1) was not accompanied by a significant change in organ weight. That DFHOPOCAM was an effective chelator was substantiated by a 28% decrease in hepatic iron with only an 8% decline in hepatic weight. Excretion of iron via the feces was increased 21% accompanied by a minor 8% fall in fecal output. Urine production was stimulated 24% concurrently with a 39% increase in urinary iron.

The higher dose of DFHOPOCAM in general evoked dose-related responses. The decrease in water imbibition was about the same order of magnitude as that seen for the low dose. Behavior and major organs were not grossly affected. Spleen weight increased 25% (low dose was 4%) and iron content fell 17% (low dose was down 11%). Liver weight fell from 8% (low dose) to 14% and liver iron decreased from 28% (low dose) to 59%. Fecal output was depressed 24% with little change in iron content. On the other hand, urinary iron rose to a modest 93% (low dose was 39%) without much of a change in urine volume (−6%).

Potency of DFHOPOCAM was about 4.5 relative to Desferal. The major route of excretion was through the kidneys, and the source of iron was predominantly the liver for both low and high doses. Of a number of compounds tested, DFHOPOCAM was least toxic to the kidneys. Results are summarized in Table 1.

and $V = 12059(12)$ Å$^3$. The large cell volume indicates eight Fe$_2$L$_3$ units per unit cell. Because of the large asymmetric unit, the structure of the monoclinic crystals was not pursued.

Precession photography of the hexagonal crystals indicated the space group to be either P6$_1$ or P6$_5$. The hexagonal needles visibly fractured several hours after being removed from solvent (density measurements suggest this is due to loss of one methanol of solvation). Thus after cleavage normal to the c-axis to give a −0.2 mm$^3$ fragment, the data crystal was mounted in a thin-walled quartz capillary and maintained at −99°±3° C. [$a = 13.731(2)$ Å, $c = 48.430(5)$ Å, and $V = 7908(2)$ Å$^3$, $z = 6$]. The 7775 unique observed data were empirically

TABLE 1

| Test Compound | Changes in splenic, hepatic, fecal and urinary iron in transfused male mice treated with potential iron chelators for several days | | | | | | | | |
|---|---|---|---|---|---|---|---|---|---|
| | Dose mg/kg | Route | Number Survivors | Toxic Signs | Percent Iron Changes vs. Control | | | | Potency vs. Standard |
| | | | | | Spleen | Liver | Feces | Urine | |
| Desferrioxamine | 250 | i.p. | 240/240 | none | ±2 | −23 | +7 | +270 | 1.0 |
| Desferrioxamine | 250 | i.p. | 150/150 | none | ±2 | −28 | +3 | +234 | 1.0 |
| DFHOPOCAM | 20 | i.p. | 10/10 | none | −11 | −28 | +21 | +39 | 4.5 |
| DFHOPOCAM | 200 | i.p. | 10/10 | water intake decreased | −17 | −59 | +4 | +93 | 0.8 |

EXAMPLE 10

Preparation of the Ferric Ion Complex of 3-HOPOCAM (Fe$_2$L$_3$, L = 3-HOPOCAM): A solution of 155 mg (0.38 mmole) of Fe(NO$_3$)$_3$9H$_2$O in 2 ml of water was added dropwise to a solution of 200 mg (0.57 mmole) of 1-hydroxy-2(1H)-pyridinone-6-carboxylic acid (Formula 7A) in 10 ml of water. A bright orange solid immediately precipitated, and the pH of the reaction mixture fell to 1.6. The pH was adjusted with 1M KOH to 7 and the precipitate was isolated by filtration and washed with water. The moist precipitate was dissolved in 15 ml of 1:1 MeOH-CH$_2$Cl$_2$, and this mixture was filtered to remove a trace of dark brown insoluble material. Evaporation of the filtrate and drying of the residue in vacuo at 25° C. gave 172 mg (78%) of amorphous orange product. IR: 1678 (s), 1609 cm$^{-1}$ (s).

Recrystallization of the Fe$_2$L$_3$ complex from dichloromethane gave elongated crystals with thin diamond-shaped cross sections. Solution NMR indicated the presence of dichloromethane, and the density (1.55 g/cm$^3$ in aqueous ZnCl$_2$) and unit cell constants (see below) were consistent with the formulation C$_{45}$H$_{42}$N$_{12}$O$_{18}$Fe$_2$.3CH$_2$Cl$_2$. Apparently some solvent was lost prior to analysis. (Analysis: C, H, N, Fe$_2$O$_3$; Cl calcd. 15.2, found 11.2.)

Orange-red hexagonal needles were obtained by evaporating a solution of amorphous material in 1:1 MeOH:CH$_2$Cl$_2$ containing a small amount (1-2%) of water. Analysis (C$_{48}$H$_{42}$N$_{12}$Fe$_2$.2CH$_3$OH.H$_2$O) C, H, N.

Crystallography: An Enraf-Nonius CAD4 diffractometer equipped with a Universal Low Temperature Device, a PDP 11/60 computer, and locally modified SDP software (see, e.g., B. A. Frenz and Assoc., "Structure Determination Package User's Guide," College Station, Texas (1982) were used. Monochromated CuK radiation ($\lambda = 1.5418$ A) was used because of the large unit cells involved for both crystal forms isolated.

Precession photography and diffractometry were used to establish the space group of the CH$_2$Cl$_2$ solvated crystals as P2$_1$/c with room temperature dimensions $a = 22.203(4)$, $b = 13.125(2)$, $c = 42.06(4)$ Å, $\beta = 79.70(4)°$ corrected for absorption; rotation around the diffraction vector gave at most a 29% variation in intensity. Crystallographic data is summarized in Table 2.

Solution of the structure indicates that the compound consists of molecules containing two high-spin ferric ions and three 3-HOPOCAM ligands arranged such that the octahedral coordination requirement of each iron atom is satisfied by the oxygen atoms of three bidentate hydroxypyridonate groups. Each 3-HOPOCAM ligand bridges between the two iron atoms.

TABLE 2

| Crystallographic summary for hexagonal crystals of Fe$_2$(C$_{15}$H$_{14}$N$_4$O$_6$)$_3$.H$_2$O. 2CH$_3$OH(C$_{47}$H$_{52}$Fe$_2$N$_{12}$O$_{21}$). | |
|---|---|
| Formula weight | 1232.7 |
| Space group | P6$_1$ |
| a (A) | 13.731(2)$^a$ |
| c (A) | 48.430(5) |
| Volume (A$^3$) | 7908(2) |
| z, formula units/cell | 6 |
| Density (calc. g/cm$^3$) | 1.553 |
| Density (obs. g/cm$^3$) | 1.51−1.55$^b$ |
| Wavelength (A) CuK$_\alpha$ | 1.5418 |
| Range of 2θ (°) | 2−120 |
| Unique reflections measured, not systematically absent | 7775 |
| Observed reflections$^c$ (n$_o$) | 5077 |
| Refined parameters (n$_v$) | 756 |
| Extinction parameter (refined) | 2.0(1) × 10$^{-7}$ |
| R$^d$ | 0.044 |
| R$_w$$^d$ | 0.049 |
| R$_{all}$$^d$ | 0.110 |
| G.O.F.$^d$ | 1.40 |
| Largest e$^-$/A$^3$ in final difference Fourier | 0.47 |

$^a$The e.s.d.'s of the last digit are shown in parentheses. Cell constants were determined from the refinement of the setting angles for 24 high angle reflections. The temperature was −99 ± 3° C.
$^b$Three density determinations by flotation were performed. In aqueous ZnCl$_2$ a value of 1.53 was obtained.
Crystals exposed to air for several months gave D = 1.51 (aqueous CsCl) suggesting loss of one methanol performula unit. The same crystals left overnight in 1:2 MeOH/H$_2$O (+CsCl) had D = 1.55.
$^c$Reflections with F$^2$ > σ(F$^2$) were considered observed and used in the least-squared refinement.
$^d$Error indices are defined as follows: R = (Σ || F$_o$| − |F$_c$||)/Σw(|f$_o$| − |F$_c$|)$^2$)/(n$_o$ − n$_v$)|$^{\frac{1}{2}}$where F$_o$ and F$_c$ are observed and calculated structure factors, the weight w$_c$ = 4F$^2$/σ$^2$(F$^2$) and the sum is over all observed reflections$^c$. R$_{all}$ is defined as is R except the sum is over all measured reflections.

EXAMPLE 11

Removal of Iron From Transferrin: The effectiveness of 3-HOPOCAM as a ferric ion chelator was evaluated in terms of its potential for removing iron from transferrin. In order to account for the effect of proton competition in the ligand strength comparisons, the relative iron-binding abilities of the ligands were ranked by the pM value, defined as $-\log [Fe^{+3}]$ of a pH 7.4 solution that is $10^{-5}$M in total ligand and $10^{-6}$M in total iron. The pM for 3-HOPOCAM was determined (by binding competition experiments with EDTA) to be 21.7, about 4 to 14 units lower than the pM value for siderophores containing three bidentate catechol or hydroxamate groups. The corresponding pM for transferrin was found to be about 23.6 (assuming $[HCO_3^-]=0.024$M), so that from a thermodynamic standpoint, 3-HOPOCAM would not be expected to be effective in in vivo iron removal from transferrin at lower (10 $\mu$M) concentrations of ligand. At the higher concentrations tested, however, the equilibrium shifted to favor the 3-HOPOCAM complex ($Fe_2L_3$), and 3-HOPOCAM did in fact remove iron from transferrin at approximately mM concentrations; in 30 min., about 29% of the iron was removed by a 1.6 mM solution of 3-HOPOCAM. Ligands incorporating more than two "HOPO" groups should be effective in removing iron from transferrin at even lower concentrations.

EXAMPLE 12

The novel chelating agents of the present invention were tested for their effectiveness in promoting excretion of $^{238}$Pu(IV) in mice as follows. Groups of five mice each received an intravenous injection of 0.2 ml of $^{238}$Pu(IV) in citrate buffer, 9250 Bq/kg body wt. One hour later 30 $\mu$mole/kg of ligand (120 $\mu$mole/kg of monomeric ligands) was injected intraperitoneally in 0.5 ml of saline. The mice were killed 24 hr after the Pu injection, frozen, and dissected after partial thawing. The $^{238}$Pu in skeleton, tissues, and separated excreta was determined by counting of the $^{234}$U L x-rays.

A test of acute toxicity was also carried out, as follows. Two mice were each given a single i.p. injection of 100, 500, or 1000 $\mu$mole/kg of ligand dissolved in 0.5 to 1.0 ml of saline at pH=7.5. Sparingly soluble ligands, dispersed by sonication, were given as finely divided suspensions. After 7 days observation, the mice were killed, selected tissues were removed and fixed for histopathological examination, and unusual findings at autopsy were recorded.

Results of the initial tests of potency and toxicity of the ligands tested are summarized in Table 3, which also includes data for the baseline ligand, $CaNa_3$-DTPA and the Pu-injected controls (no ligands) killed at 1 hr or 24 hr after injection. Results using iron and zinc complexes of the ligands are summarized in Table 4. As illustrated by the data compiled in Tables 3 and 4, all the novel chelating agents provided effective Pu removal, although HOPO-substituted desferrioxamine proved to be the most effective Pu removal agent (86% of newly injected Pu excreted in 24 hr). Furthermore, none of the desferrioxamine derivatives proved to be acutely toxic, even at the relatively high dose of 1000 $\mu$mole/kg.

TABLE 3

| | Percent of injected $^{238}$Pu ± S.D. at 24 hr[b,c] | | | | | | |
|---|---|---|---|---|---|---|---|
| | Tissues | | | | | Excreta | |
| | Liver | Skeleton | Kidneys | Residual soft tissue | Body content | Urine | Feces and GI contents |
| Test Legands | | | | | | | |
| 3,4,3-HOPOCAM* | 8.9 ± 1.7 | 7.5 ± 0.7 | 0.2 | 1.6 ± 0.6 | 19 | 24. | 57 |
| 3,4-HOPOCAM* | 17. ± 4.6 | 9.5 ± 3.5 | 0.6 | 5.6 ± 1.2 | 36 | 7.5 | 56 |
| HOPO—MECAM** | 18. ± 6.3 | 17. ± 2.5 | 1.8 | 10. ± 1.8 | 46 | 9.6 | 44 |
| 3-HOPOCAM | 8.7 ± 1.2 | 17. ± 2.8 | 1.4 | 11. ± 0.8 | 38 | 8.7 | 53 |
| HOPO—$CO_2$H | 52. ± 4.6 | 24. ± 5.1 | 1.2 | 6.3 ± 1.6 | 83 | 7.0 | 9.6 |
| HOPO—$COMe_2$ | 56. ± 6.3 | 27. ± 5.5 | 1.4 | 5.9 ± 1.2 | 87 | 4.5 | 8.6 |
| DFHOPOCAM | 4.6 ± 1.2 | 7.4 ± 0.8 | 0.3 | 1.7 ± 0.3 | 14 | 40 | 46 |
| Baseline Ligand | | | | | | | |
| $CaNa_3$—DTPA | 16 ± 2.8 | 11 ± 1.2 | 0.4 | 3.8 ± 1.5 | 30 | 70 | |
| $^{238}$Pu-injected Controls | | | | | | | |
| 1-hr Controls | 30 ± 7.4 | 24 ± 4.4 | 2.7 | 37 ± 7.1 | 94 | 1.1 | 4.8 |
| 24-hr Controls | 49 ± 8.3 | 32 ± 7.9 | 20 | 7.7 ± 2.0 | 92 | 4.7 | 4.1 |
| Desferrioxamine | 19 ± 13 | 20 ± 11 | 1.8 | 4.5 ± 1.4 | 46 | 40 | 15 |

[a]Single or double asterisks indicate acutely toxic (50% to 100% lethality) in 7 days after a single i.p. injection of 1000 or 500 $\mu$mole/kg, respectively.
[b]S.D. = $[\Sigma dev^2/(n-1)]^{\frac{1}{2}}$. Where S.D. is not shown, samples were pooled for 5-mouse group. Data were normalized to 100% material recovery; discrepancies are due to rounding.
[c]Ligand was administered (30 $\mu$mole/kg, i.p.) at 1 hr and mice were killed at 24 hr after injection (i.v.) of $^{238}$Pu(IV) citrate. Dosage of monomers, HOPO—$CO_2$H and HOPO—$COMe_2$, was 120 $\mu$mole/kg.

TABLE 4

| | Percent of injected $^{238}$Pu ± S.D. at 24 hr[b,c] | | | | | | |
|---|---|---|---|---|---|---|---|
| | Tissues | | | | | Excreta | |
| | Liver | Skeleton | Kidneys | Residual soft tissue | Body content | Urine | Feces and GI contents |
| Test Legands | | | | | | | |
| Iron Complex | | | | | | | |
| 3,4,3-HOPOCAM—Fe | 5.1 ± 2.2 | 6.0 ± 0.5 | 0.1 | 2.3 ± 0.5 | 13 | 19 | 68 |
| Zinc Complexes | | | | | | | |
| 3,4,3-HOPOCAM—Zn** | 4.0 ± 0.8 | 9.6 ± 0.6 | 0.3 | 2.4 ± 0.6 | 16 | 21 | 63 |
| 3,4-HOPOCAM—Zn** | 13. ± 3.8 | 12. ± 2.2 | 3.1 | 5.1 ± 1.4 | 34 | 14 | 52 |

TABLE 4-continued

| | Percent of injected $^{238}$Pu ± S.D. at 24 hr[b,c] | | | | | | |
|---|---|---|---|---|---|---|---|
| | Tissues | | | | Excreta | | |
| | Liver | Skeleton | Kidneys | Residual soft tissue | Body content | Urine | Feces and GI contents |
| 3-HOPOCam—Zn** Native Ligand | 5.5 ± 0.8 | 16. ± 2.4 | 0.4 | 12. ± 2.6 | 35 | 5.2 | 60 |
| 3,4,3-HOPOCAM* | 8.9 ± 1.7 | 7.5 ± 0.7 | 0.2 | 1.6 ± 0.6 | 19 | 24 | 57 |

[a]Single or double asterisks indicate acutely toxic (50% to 100% lethality) in 7 days after a single i.p. injection of 1000 or 500 μmole/kg. respectively.
[b]S.D. = [Σ dev²/(n - 1)]^(1/2). Where S.D. is not shown, samples were pooled for 5-mouse group. Data were normalized to 100% material recovery; discrepancies are due to rounding.
[c]Ligand was administered (30 μmole/kg, i.p.) at 1 hr. and mice were killed at 24 hr. after injection (i.v.) of $^{238}$Pu(IV) citrate.

While the various aspects of the inventive compounds and processes have been described in conjunction with the preferred specific embodiments thereof, it is to be understood that all synthetic steps, reagents and reaction conditions reasonably equivalent to those described explicitly are also within the scope of this invention, as are all reasonably equivalent structures. The description given above is intended to be illustrative and not limitative of the various embodiments of this invention, the scope of which is defined by the appended claims.

We claim:

1. A chelating agent having the structure:

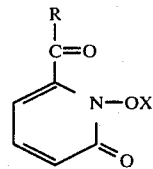

wherein R is a hydroxy group or

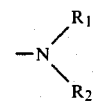

where $R_1$ and $R_2$ are selected from the group consisting of H, —CH$_3$, —CH$_2$CH$_3$ and —CH$_2$—φ, and X is either hydrogen, an alkali metal ion, or a quaternary ammonium ion.

2. The chelating agent of claim 1, wherein R is

* * * * *